(12) United States Patent
Wang et al.

(10) Patent No.: US 12,288,327 B2
(45) Date of Patent: Apr. 29, 2025

(54) IMAGE-DRIVEN BRAIN ATLAS CONSTRUCTION METHOD, APPARATUS, DEVICE AND STORAGE MEDIUM

(71) Applicant: SHENZHEN INSTITUTES OF ADVANCED TECHNOLOGY, Guangdong (CN)

(72) Inventors: Shuqiang Wang, Guangdong (CN); Qiankun Zuo, Guangdong (CN); Min Gan, Guangdong (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 0 days.

(21) Appl. No.: 17/764,446

(22) PCT Filed: Feb. 3, 2021

(86) PCT No.: PCT/CN2021/075096
§ 371 (c)(1),
(2) Date: Mar. 28, 2022

(87) PCT Pub. No.: WO2022/147871
PCT Pub. Date: Jul. 14, 2022

(65) Prior Publication Data
US 2023/0342918 A1    Oct. 26, 2023

(30) Foreign Application Priority Data
Jan. 9, 2021   (CN) .......................... 202110026756.3

(51) Int. Cl.
G06T 7/00    (2017.01)
G16H 50/20   (2018.01)

(52) U.S. Cl.
CPC .......... *G06T 7/0012* (2013.01); *G16H 50/20* (2018.01); *G06T 2207/10088* (2013.01);
(Continued)

(58) Field of Classification Search
CPC ......... G06T 7/0012; G06T 2207/10088; G06T 2207/20081; G06T 2207/20084; G06T 2207/30016; G06H 50/20
See application file for complete search history.

(56) References Cited

U.S. PATENT DOCUMENTS

| 2016/0220821 A1* | 8/2016 | O'Connell ............. A61B 5/318 |
| 2017/0151436 A1* | 6/2017 | Flaherty ............... A61B 5/0531 |
| 2021/0240265 A1* | 8/2021 | Pilly ..................... G06F 3/015 |

FOREIGN PATENT DOCUMENTS

| CN | 106203470 A | 12/2016 |
| CN | 107731283 A | 2/2018 |

(Continued)

OTHER PUBLICATIONS

Cite for NPL—Banka A. et al., Multi-View Brain HyperConnectome AutoEncoder For Brain State Classication, International Workshop on PRedictive Intelligence In MEdicine, Oct. 2020.

*Primary Examiner* — John J Lee
(74) *Attorney, Agent, or Firm* — Brooks Kushman P.C.

(57) ABSTRACT

The present application is applicable to the field of medical imaging technologies, and provides an image-driven brain atlas construction method and apparatus, a device and a storage medium. The method includes: acquiring multi-modal data of a brain to be predicted, where the multi-modal data is acquired according to image data collected when the brain is under at least three different modalities; inputting the multi-modal data into a preset fusion network for processing to output and acquire feature parameters of the brain; where the processing of the multi-modal data by the fusion network includes: extracting a non-Euclidean spacial feature and an Euclidean spacial feature of the multi-modal data, and performing hypergraph fusion on the non-Euclidean spacial feature and the Euclidean spacial feature to acquire the feature parameters, where the feature parameters are used to (Continued)

characterize a brain connection matrix and/or a disease category of the brain.

20 Claims, 8 Drawing Sheets

(52) U.S. Cl.
CPC .............. *G06T 2207/20081* (2013.01); *G06T 2207/20084* (2013.01); *G06T 2207/30016* (2013.01)

(56) References Cited

FOREIGN PATENT DOCUMENTS

| | | |
|---|---|---|
| CN | 109492691 A | 3/2019 |
| CN | 111860951 A | 10/2020 |
| CN | 111881350 A | 11/2020 |

\* cited by examiner

IMAGE-DRIVEN BRAIN ATLAS CONSTRUCTION METHOD, APPARATUS, DEVICE AND STORAGE MEDIUM

CROSS-REFERENCE TO RELATED APPLICATIONS

The present application is a national stage of International Application No. PCT/CN2021/075096 filed on Feb. 3, 2021, which claims priority of Chinese Patent Application No. 202110026756.3 filed on Jan. 9, 2021, the contents each of which are incorporated herein by reference thereto in its entirety.

TECHNICAL FIELD

The present application involves in the field of medical imaging technologies, and particularly relates to an image-driven brain atlas construction method, an image-driven brain atlas construction apparatus, a device and a storage medium.

BACKGROUND

With development of medical imaging technologies, different modalities of data can describe information of a certain disease in a brain, which can be used to assist disease diagnosis and treatment. However, the information provided by data having a single modality is often limited, therefore, acquisition of fused features by fusing different modalities of data has currently become a popular research direction.

At present, a commonly used modal fusion method is to directly fuse the different modalities of data by means of weighted summation. However, there may be heterogeneity between the different modalities of data, which makes it impossible to accurately extract the fusion features of the different modalities of data, so that it is impossible to construct an accurate brain atlas, thereby resulting in wrong determination of the disease diagnosis.

SUMMARY

The present application provides an image-driven brain atlas construction method, an image-driven brain atlas construction apparatus, a device and a storage medium, so as to solve the problem that: it is impossible to accurately extract the fusion features of the different modalities of data since there may be heterogeneity between the different modalities of data, so that it is impossible to construct an accurate brain atlas, thereby resulting in wrong determination of the disease diagnosis.

A first aspect of the present application provides an image-driven brain atlas construction method, which includes: acquiring multi-modal data of a brain to be predicted, where the multi-modal data is acquired according to image data collected when the brain is under at least three different modalities; inputting the multi-modal data into a preset fusion network for processing to output and acquire feature parameters of the brain; where the processing of the multi-modal data by the fusion network includes: extracting a non-Euclidean spacial feature and an Euclidean spacial feature of the multi-modal data, and performing hypergraph fusion on the non-Euclidean spacial feature and the Euclidean spacial feature to acquire the feature parameters, where the feature parameters are used to characterize a brain connection matrix and/or a disease category of the brain.

Optionally, the performing hypergraph fusion on the non-Euclidean spacial feature and the Euclidean spacial feature to acquire the feature parameters includes: performing hypergraph data transformation on the non-Euclidean spacial feature and the Euclidean spacial feature respectively to acquire a first hypergraph matrix and a second hypergraph matrix; performing vertex convolution calculation on the first hypergraph matrix and the second hypergraph matrix respectively to acquire a first hyperedge feature and a second hyperedge feature; performing hyperedge convolution calculation on the first hyperedge feature and the second hyperedge feature to acquire a fused feature; acquiring the feature parameters according to the fused feature.

Optionally, the performing hyperedge convolution calculation on the first hyperedge feature and the second hyperedge feature to acquire a fused feature includes: merging the first hyperedge feature with the second hyperedge feature to acquire a merged matrix; performing hyperedge convolution calculation on the merged matrix to acquire the fused feature.

Optionally, the image data includes sMRI data, DTI data and fMRI data of the brain;
the multi-modal data includes a node connection matrix acquired according to the DTI data, a node feature matrix acquired according to the fMRI data and the sMRI data.

Optionally, the extracting the non-Euclidean spatial feature of the multi-modal data includes: performing graph convolution processing on the node connection matrix and the node feature matrix to acquire the non-Euclidean spatial feature.

Optionally, the extracting the Euclidean spatial feature of the multi-modal data includes: performing convolution processing on the sMRI data to acquire a semantic representation vector; encoding the semantic representation vector to acquire the Euclidean spatial feature.

Optionally, the method further includes: acquiring data samples, where the data samples include sMRI data, DTI data, fMRI data of a sample brain and disease category labels of the sample brain; acquiring a node feature matrix, a node connection matrix and a prior probability distribution of the sample brain according to the fMRI data and the DTI data of the sample brain; acquiring a node feature of a hidden layer space from the prior probability distribution through sampling; conducting adversarial training on a preset adversarial generative hypergraph fusion network by using the node feature of the hidden layer space, the node feature matrix, the node connection matrix and the sMRI data of the sample brain; when the adversarial generative hypergraph fusion network converges, performing migration processing on the adversarial generative hypergraph fusion network to acquire the fusion network.

A second aspect of the present application provides an image-driven brain atlas construction apparatus, which includes:
an acquisition unit configured to acquire multi-modal data of a brain to be predicted, where the multi-modal data is acquired according to image data collected when the brain is under at least three different modalities;
a prediction unit configured to input the multi-modal data into a preset fusion network for processing to output and acquire feature parameters of the brain; where the processing of the multi-modal data by the fusion network comprises: extracting a non-Euclidean spacial feature and an Euclidean spacial feature of the multi-modal data, and performing hypergraph fusion on the non-Euclidean spacial feature and the Euclidean spacial feature to acquire the feature parameters, where the feature parameters are used to characterize a brain connection matrix and/or a disease category of the brain.

A third aspect of the present application provides a terminal device, which includes a memory, a processor and a computer program stored in the memory and executable on the processor, and the processor, when executing the computer program, implements the method of the first aspect or any optional implementation of the first aspect.

A fourth aspect of the present application provides a computer-readable storage medium on which a computer program is stored, and the computer program, when executed by a processor, implements the method of the first aspect or any optional implementation of the first aspect.

A fifth aspect of the present application provides a computer program product, and the computer program product, when executed on a terminal device, causes the terminal device to implement the method of the first aspect or any optional implementation of the first aspect.

It could be understood that, the beneficial effects of the second aspect to the fifth aspect may refer to relevant description in the first aspect, which will not be repeated here again.

Compared with the prior art, the beneficial effects of the embodiments of the present application lie in that:

based on the method provided in the present application, firstly the non-Euclidean spatial feature and the Euclidean spatial feature are extracted from the multi-modal data, and then the features of different spaces are mapped into the hypergraph data structure for hypergraph fusion, to avoid the possibility heterogeneity of the features of difference spaces, so as to acquire the complementary fused feature between the multi-modal data. Therefore, the feature parameters determined by this fused feature can describe the relevant information inside the brain more accurately and abundantly, so that the brain atlas represented by the feature parameters is also more accurate, thereby reducing the wrong determination rate of disease diagnosis.

BRIEF DESCRIPTION OF THE DRAWINGS

In order to illustrate the technical solutions in the embodiments of the present application more clearly, the drawings that need to be used in the description for the embodiments or the prior art will be briefly introduced below. Obviously, the drawings in the following description are only some embodiments of the present application, and other drawings may also be obtained for those of ordinary skill in the art based on these drawings without any creative effort.

DETAILED DESCRIPTION

At present, due to possible heterogeneity between the different modalities of data, it is impossible to accurately extract fused features of the different modalities of data, thereby resulting in the problem of wrong determination of disease diagnosis. The present application provides a method for predicting feature parameters based on multi-modal data, in which the possible heterogeneity between the features from different spaces is avoided through extracting non-Euclidean spatial features and Euclidean spatial features from the multi-modal data and then mapping the features from the different spaces to a hypergraph data structure for hypergraph fusion, thereby complementary fused features between the multi-modal data can be acquired.

The technical solutions of the present application will be described in detail below with specific embodiments. The following specific embodiments may be combined with each other, and the same or similar concepts or processes may not be repeated in some embodiments.

Figure 1:
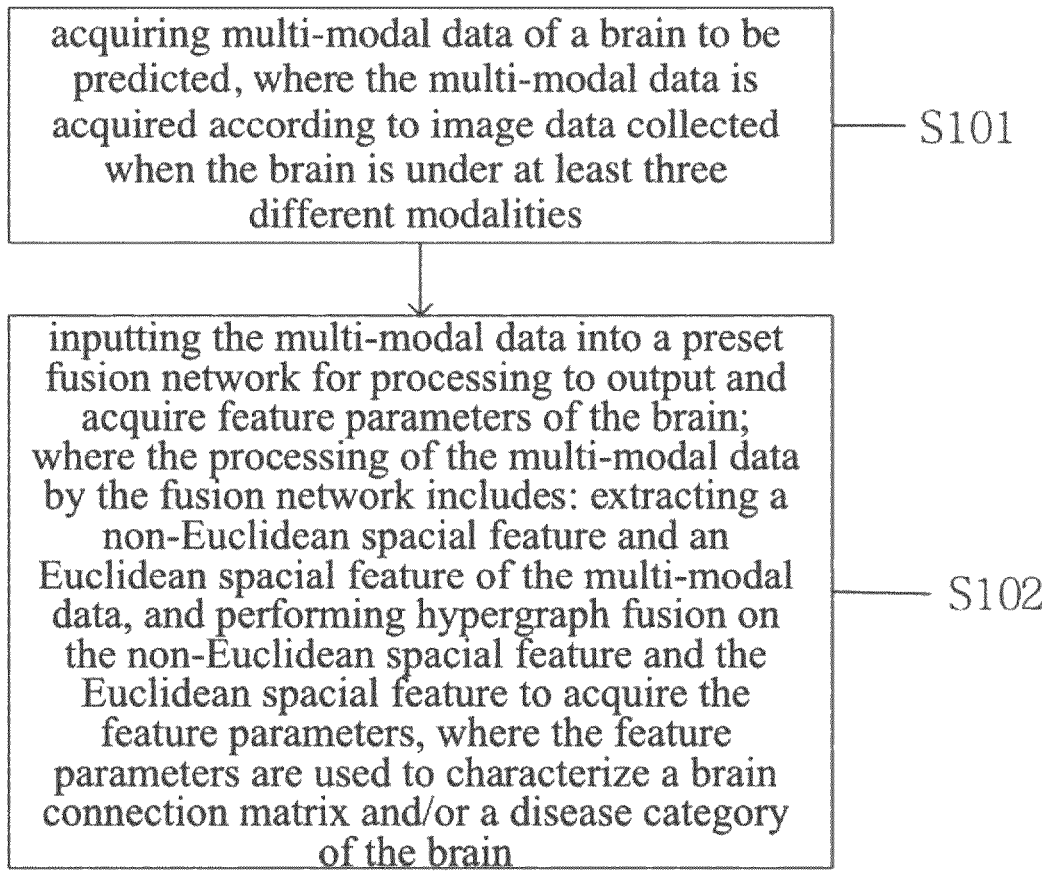
FIG. 1 is a flowchart of an example of an image-driven brain atlas construction method provided by an embodiment of the present application.

Referring to in FIG. 1, FIG. 1 is a flowchart of an embodiment of an image-driven brain atlas construction method provided by the present application, an execution subject of this method may be an image data acquisition device, for example, a terminal deice such as a PET (Positron Emission Computed Tomography) device, a CT (Computed Tomography) device, a MRI (Magnetic Resonance Imaging) device, etc. It may also be a terminal device such as a control device of an image data acquisition device, a computer, a robot, a mobile terminal and the like. As shown in FIG. 1, the method includes the following.

At S101, acquire multi-modal data of a brain, where the multi-modal data is acquired according to image data which is collected when the brain is under at least three different modalities.

Here, the image data may be PET image data, CT image data, or MRI image data, or the like.

In an embodiment of the present application, the image data collected under at least three different modalities may be collected based on an Euclidean space and a non-Euclidean space, respectively.

Exemplarily, taking the MRI image data acquired by an MRI device as an example, the at least three different modalities of MRI image data may include sMRI (Structural Magnetic Resonance Imaging) data acquired based on the Euclidean space and fMRI (Functional Magnetic Resonance Imaging), and DTI (Diffusion Tensor Imaging) data acquired based on the non-Euclidean space.

Among them, the sMRI data can reflect tissue structures of the brain, so as to locate a local tissue having lesions or abnormality in the brain. The fMRI data is feature data of functional pulses of different positions of the brain collected by the MRI device over time when a subject is performing a certain task or not performing a task. The DTI is dispersion degree data of water molecules in the brain collected by the MRI device, the dispersion degree of the water molecules in the brain can reflect characteristics of an institution where the water molecules are located. The DTI can effectively observe and track a fiber tract (eg, a myocardial fiber tract, a brain protein fiber tract, etc.), which reflects the topology of the brain.

Correspondingly, the multi-modal data acquired based on the sMRI data, the DTI data and the fMRI data includes a node connection matrix acquired according to the DTI data, a node feature matrix acquired according to the fMRI data and the sMRI data.

Among them, the node connection matrix may be a matrix A with a size of m×m, which is used to represent fiber tract density between m (m>1, m is an integer) functional nodes in the brain. The node connection matrix is also commonly referred to as structural connection features or a structure connection atlas of a brain region. Exemplarily, for the brain, after the DTI data of the brain is acquired, the DTI data may be input into PANDA software for preprocessing to acquire the fiber tract data of the white matter of the brain. Then, based on AAL (Anatomical Automatic Labeling) templates, a fiber tract network among multiple brain regions is constructed to acquire the fiber tract density among the brain regions. Among them, one brain region is one functional node of the brain.

The node feature matrix may be a matrix X with a size of m×d, which is used to characterize a node feature of each functional node, where d (d>1, d is an integer) represents the length of the node feature of each functional node. The node feature includes feature data collected by the functional pulse of the functional node at d consecutive sampling points, which can also be referred to as a time sequence of the functional node. The node feature matrix is also commonly referred to as a functional connection feature or a functional connection atlas of the brain region. Exemplarily, for the brain, after the fMRI data of the brain is acquired, the fMRI data may be input into the GRETNA software for preprocessing, and then the preprocessed fMRI data may be mapped to the AAL templates to obtain the time sequence of each brain region.

m and d may be set according to actual needs. For example, for the brain, after the brain regions are divided by the AAL templates, the density of fiber tracts corresponding to 90 brain regions in the cerebral cortex may be selected as the node connection matrix A, and the time sequences corresponding to the 90 brain regions may be selected as the node feature matrix X.

At S102, input the multi-modal data into a preset fusion network for processing to output and acquire feature parameters of the brain; the processing of the multi-modal data by the fusion network includes: extracting non-Euclidean spatial features and Euclidean spatial features of the multi-modal data, and performing hypergraph fusion on the non-Euclidean spatial features and the Euclidean spatial features to acquire the feature parameters, where the feature parameters are used to characterize the brain connection matrix and/or disease category of the brain.

Exemplarily, the feature parameters may include a first feature parameter and/or a second feature parameter, among them, the first feature parameter is used to characterize the brain connection matrix of the brain. The first feature parameter may be a matrix with a size of m×m. The brain atlas presented based on the brain connection matrix may be used to analyze an abnormal brain connection feature of a patient, thereby assisting a doctor to give a more accurate diagnosis suggestion and medical measure.

The second feature parameter is used to characterize a lesion category of the brain. For example, a disease category targeting the Alzheimer's disease in the brain may be divided into four disease categories including AD (Alzheimer's disease), LMCI (late mild cognitive impairment), EMCI (early mild cognitive impairment), and normal elderly (Normal). The second feature parameter may be a vector with a size of 1×4, and each parameter in this vector represents probability of one of the four disease categories respectively. The probability of the lesion is also a representation manner of the brain atlas.

Figure 2:
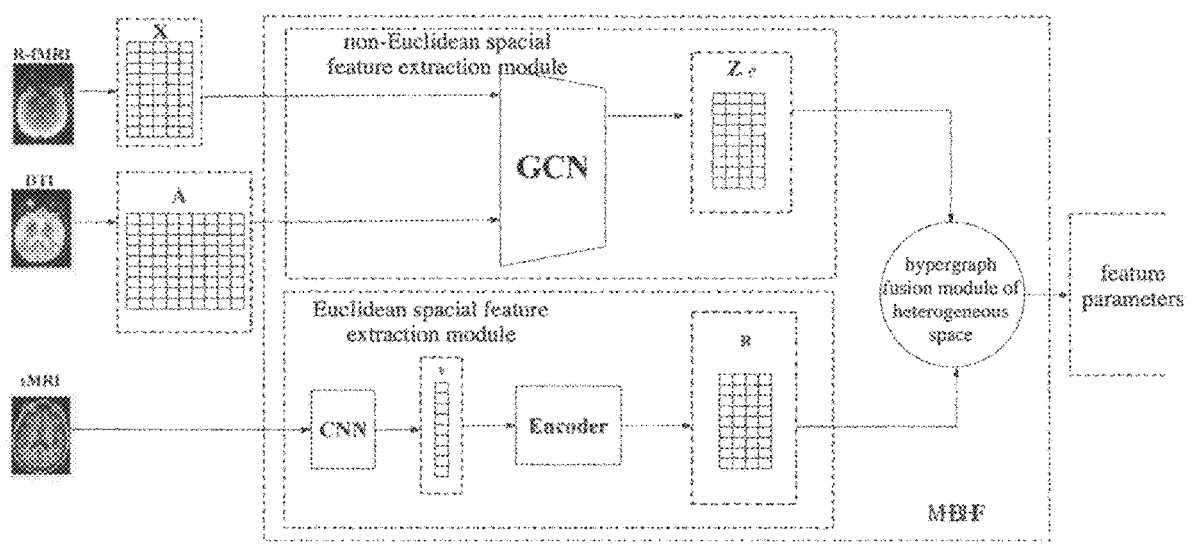
FIG. 2 is a network structure diagram of a fusion network provided by an embodiment of the present application.

As shown in FIG. 2, the fusion network provided by the present application includes a non-Euclidean spacial feature extraction module, an Euclidean spacial feature extraction module, and a heterogeneous-based hypergraph fusion module. This fusion network may be called a MHBHF (multi-modal heterogeneous-Based Hypergraph Fusion) network.

Among them, the non-Euclidean spacial feature extraction module is configured to extract a non-Euclidean spatial feature Z from the multi-modal data, which represents a correlation feature between different modalities of data.

In one example, the non-Euclidean spatial feature extraction module may include a graph convolutional network (GCN model). Through inputting the node connection matrix A and the node feature matrix X in the multi-modal data into the GCN model, the node connection matrix A and the node feature matrix X are encoded to acquire a node feature representation (i.e., Z') of a hidden layer space. Among them, the encoding process of the node connection matrix A and the node feature matrix X based on the GCN model includes using the node connection matrix A to perform weighted aggregation on the node feature matrix X, and then performing dimension reduction processing to obtain the node feature representation Z' of the hidden layer space with a size of m×q, where q is the length of the node feature of the hidden layer space, and d>q≥1.

It could be understood that the non-Euclidean spatial feature Z' is a latent connection feature extracted through mutually mapping, by the GCN model, the structural connection features with the functional connection features, which represents an incidence feature between the node connection matrix A and the node feature matrix X.

The Euclidean spatial feature extraction module is configured to extract an Euclidean spatial feature R from the multi-modal data. In one example, the Euclidean spatial feature extraction module may include a trained convolutional neural network (CNN model) and an encoder. Through inputting the sMRI data into the CNN model for processing, a feature vector v is obtained; then the feature vector v is input into the encoder for processing to obtain the Euclidean spatial feature R. Among them, the Euclidean space feature R is the feature representation of the hidden layer space corresponding to the non-Euclidean space feature and extracted based on the Euclidean space, and the size of R is m×q. The encoder may be an encoder part of an encoder-decoder model.

It can be seen that the incidence feature can be extracted from the DTI data and the fMRI data based on the non-Euclidean spatial feature extraction module, and the node features of the hidden layer spaces of the functional nodes can be extracted from the sMRI data based on the Euclidean spatial feature extraction module, which increases the richness of the feature extraction, and can effectively improve the accuracy of subsequent feature parameter prediction.

Figure 3:
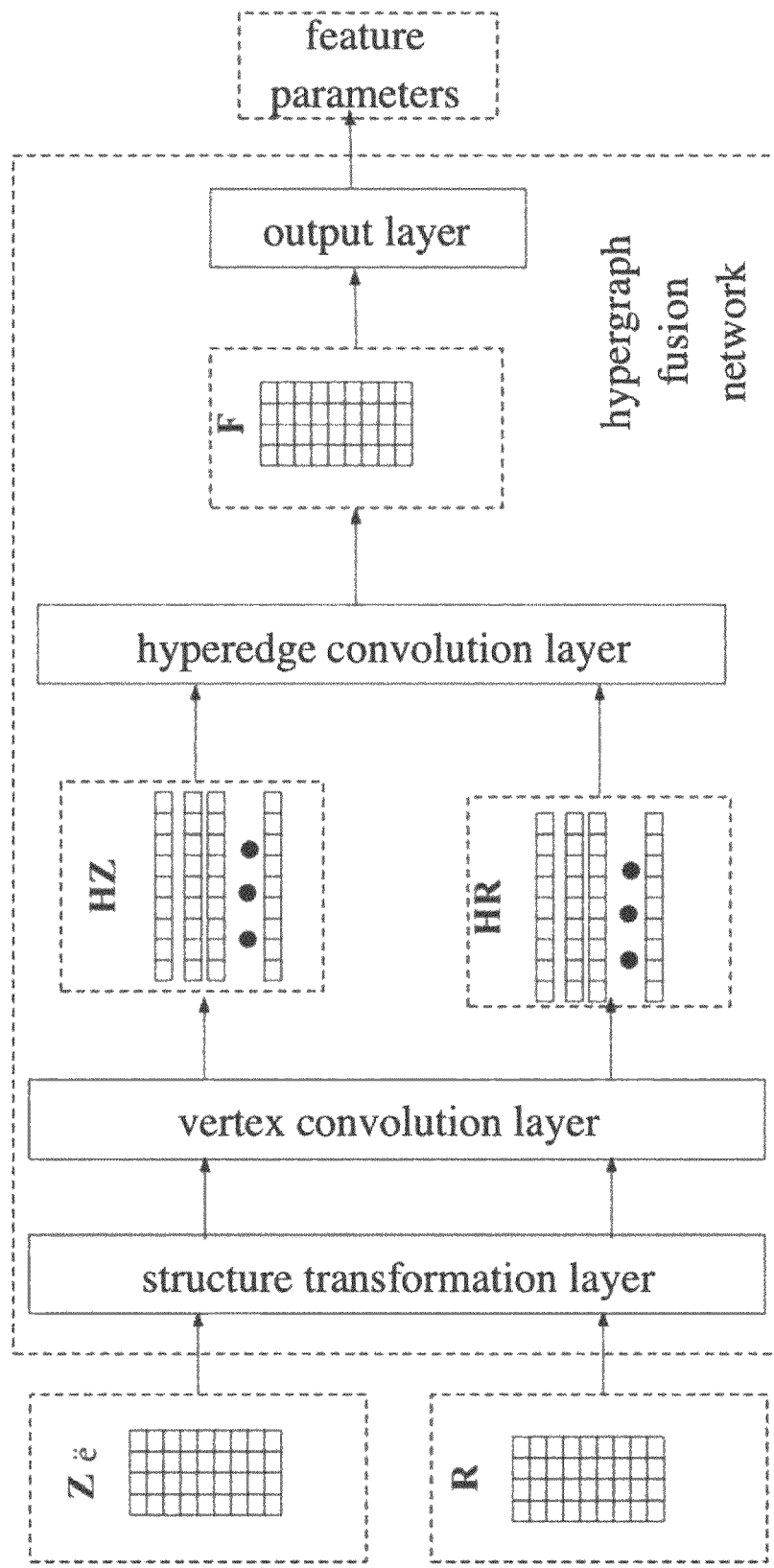
FIG. 3 is a network structure diagram of a hypergraph fusion network provided by an embodiment of the present application.

The hypergraph fusion module of the heterogeneous space is configured to fuse the non-Euclidean spacial feature Z' and the Euclidean spacial features R to obtain the feature parameters. In one example, the heterogeneous-based hypergraph fusion module may include a trained hypergraph fusion network. A network structure of the hypergraph fusion network may be as shown in FIG. 3, after Z' output by the non-Euclidean spatial feature extraction module and R output by the Euclidean spatial feature extraction module are input into a structure transformation layer of the hypergraph fusion network, the structure transformation layer performs hypergraph structure transformation on Z' and R respectively, to transform Z' into a first hypergraph matrix $G_z$ with a size of m×m and transform R into a second hypergraph matrix $G_R$ with a size of m×m. Exemplarily, the hypergraph structure transformation may be implemented based on a KNN (k-nearest neighbor classification) algorithm.

Then, the obtained $G_z$ and $G_R$ are input to a vertex convolution layer for vertex convolution calculation, and a hyperedge feature is obtained according to hypergraph structure aggregation of m functional nodes. That is, the vertex convolution calculation is performed on $G_z$ to obtain a first hyperedge feature $H_z$, and the vertex convolution calculation is performed on $G_R$ to obtain a second hyperedge feature $H_R$. Exemplarily, the vertex convolution calculation may be implemented according to the following formula:

$$H = D_e^{-1/2} G^T D_e^{-1/2} Y W$$

Where, when H represents $H_z$, G represents $G_z$, Y represents Z', and $D_e$ represents hyperedge freedom degree of $G_z$; when H represents $H_R$, G represents $G_R$, Y represents R, and $D_e$ represents hyperedge freedom degree of $G_R$; W is a vertex convolution parameter obtained through training, W has a size of d×d, and $D_e$ has a size of m×m.

After $H_z$ and $H_R$ are obtained, $H_z$ and $H_R$ may be input into a hyperedge convolution layer, and hyperedge convolution calculations may be performed on the obtained $H_z$ and $H_R$ according to the following formula to obtain a fused feature F (with a size of m×d) of Z' and R.

$$F = D_v^{-1/2} G^T D_v^{-1/2} H'$$

Where, H' is a merged matrix with a size of 2 m×d which is obtained after $H_z$ and $H_R$ are merged, and $D_v$ represents a matrix with a size of m×2 which is obtained by superposing node freedom degrees of $G_R$ and $G_z$.

After the fused feature F is obtained, F is input into an output layer of the hypergraph fusion network, and the feature parameters are obtained through the processing of the output layer.

Exemplarily, the output layer may include a classifier, and the classifier performs feature fusion on F after the output layer inputs F into the classifier to obtain the first feature parameter. For example, for the Alzheimer's disease of the brain, the classifier may be a 4-classifier. After F is input into the classifier, the classifier performs feature fusion on F and outputs a vector with a size of 1×4, which is used to describe probability of each disease category in the Alzheimer's disease of the brain predicted by the fusion network.

Alternatively, the output layer may perform matrix transformation on F to obtain a matrix $\sigma(FF^T)$ with a size of m×m, i.e. the second feature parameter (brain connection matrix). Here, $\sigma(\ )$ is a mapping function, which is used to map each value in the matrix $FF^T$ to a value between 0 and 1.

Alternatively, after receiving the fused feature F, the output layer may input F into the classifier to perform feature fusion to output the first feature parameter, and perform matrix transformation on F to output the second feature parameter.

Based on this hypergraph fusion network, through mapping the features in different spaces to the hypergraph data and fusing the features in different spaces by using the hypergraph convolution strategy, the possible heterogeneity between the features in different spaces is avoided, so that the complementary fused features between the different modalities of data are acquired.

It can be seen that based on the fusion network provided by the present application, the extraction of incidence features and the extraction of complementary features between different modalities of data can be realized, and the feature parameters (including the first feature parameter and/or the second feature parameter) can be obtained based on the extracted fused features. The brain connection matrix obtained based on the first feature parameter is provided with richer connection feature information, for example, in addition to simple structural connection features and functional connection features, it is also provided with the complementary connection information and incidence connection information between the structural connection features and the functional connection features. Therefore, the brain connection matrix can provide more effective disease information, so as to improve the accuracy of disease diagnosis based on the brain connection matrix. Correspondingly, since the second feature parameter is more accurate, it can more accurately reflect the lesion category of the brain.

With regard to the fusion network provided by the present application, the present application further provides an adversarial collaborative training method to implement training on the network parameters involved in each module. A dataset including the sMRI data, DTI data and fMRI data of the brain and the corresponding disease category labels of the Alzheimer's disease in the brain is taken as an example below to illustrate the training process of the fusion network.

Here, the dataset includes multiple sets of data samples, and each set of data samples includes sMRI data, DTI data and fMRI data collected from a subject's brain, as well as the subject's disease category labels. For example, multiple Alzheimer's disease (AD) patients, multiple late-stage mild cognitive impairment (LMCI) patients, multiple early-stage mild cognitive impairment (EMCI) patients, and multiple normal elderly (Normal) patients may be selected as subjects. The brain image data (including the sMRI data, the DTI data and the fMRI data) of each of the subjects is collected separately, and disease category labels are marked on the image data of each of the subjects. Among them, the disease category labels are diagnostic information obtained through clinical observation and diagnosis of the subject by a professional doctor. A portion of the dataset (e.g., 90%) may be selected as a training set. The training of the fusion network is completed by using multiple sets of data samples in the training set. The remaining portion is used as a test set to test the trained fusion network for performance testing and optimization.

First, an adversarial generative hypergraph fusion network is set up. The adversarial generative hypergraph fusion network includes a non-Euclidean spatial feature extraction network, an sMRI feature extraction network, an Euclidean spatial feature extraction network, and an initial hypergraph fusion network.

Among them, the non-Euclidean spatial feature extraction network is configured to obtain a GCN model in the fusion network through training. The sMRI feature extraction network is configured to acquire a CNN model in the fusion network through training. The Euclidean spatial feature extraction network is configured to acquire an encoder in the fusion network through training. The initial hypergraph fusion network is configured to acquire a hypergraph fusion network in the fusion network through training.

Figure 4:
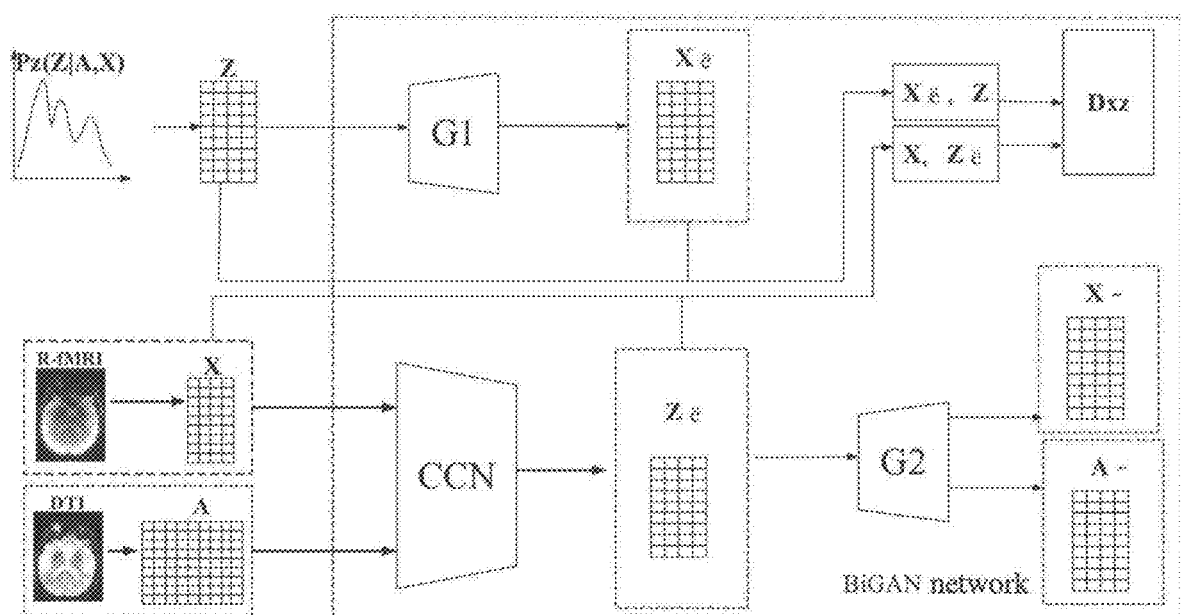
FIG. 4 is a network structure diagram of a BiGAN (Bidirectional Generative Adversarial Network) provided by an embodiment of the present application.

Exemplarily, the non-Euclidean spatial feature extraction network may perform network parameter training for a BiGAN ((Bidirectional Generative Adversarial Network) as shown in FIG. 4. As shown in FIG. 4, the BiGAN network includes a GCN model, a generator G1, a generator G2, and a discriminator Dxz. Among them, the GCN model is an encoder in the BiGAN network.

Figure 5:
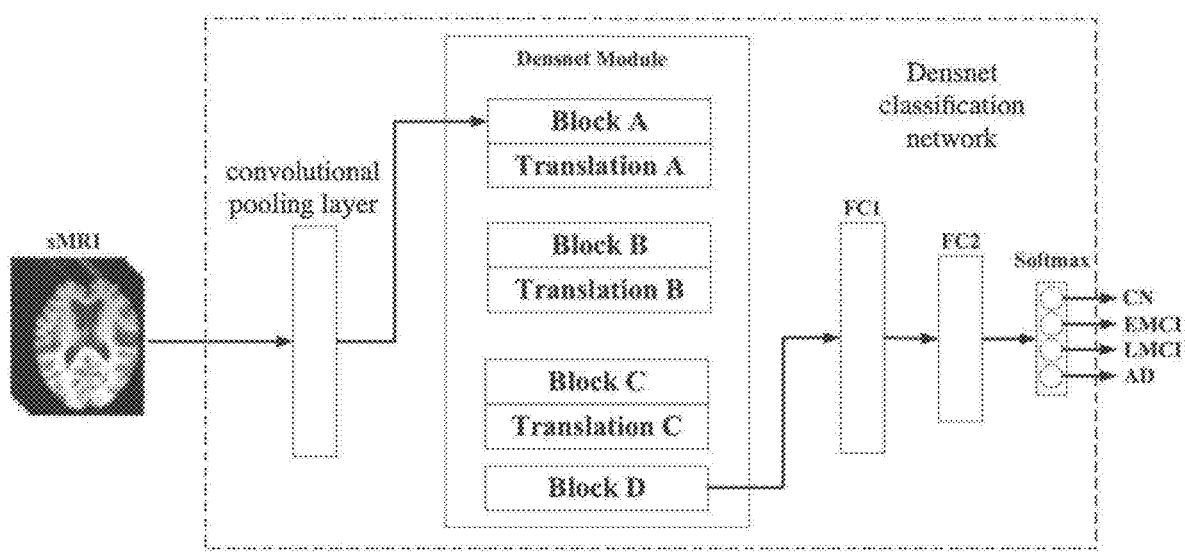
FIG. 5 is a network structure diagram of a Densnet classification network provided by an embodiment of the present application.

The sMRI feature extraction network may be any CNN model. In order to make full use of the feature information of the Euclidean space, reduce the computational complexity of the model and improve the training efficiency, a Densnet classification network (which is a kind of CNN model having a simple network structure) is taken as an example below for illustration. As shown in FIG. 5, the Densenet classification network includes a convolution pooling layer, a Densnet module, a fully connected layer FC1, a fully connected layer FC2, and a Softmax function.

Figure 6:
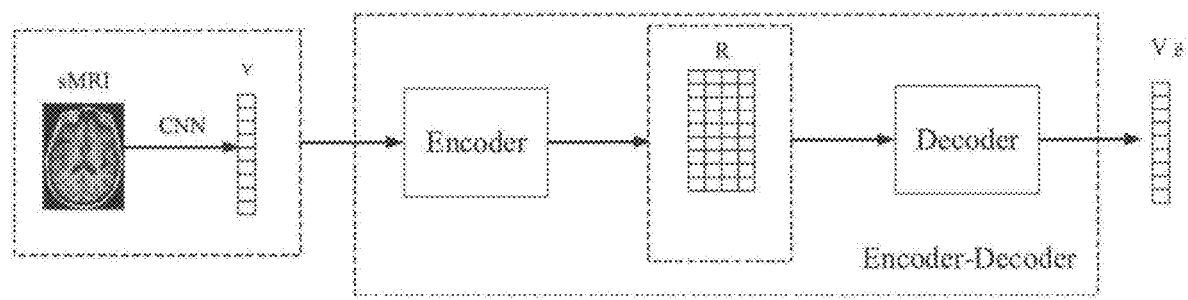
FIG. 6 is a network structure diagram of an encoder-decoder model provided by an embodiment of the present application.

The Euclidean spatial feature extraction network may be as shown in FIG. 6, which includes an encoder-decoder model.

Figure 7:
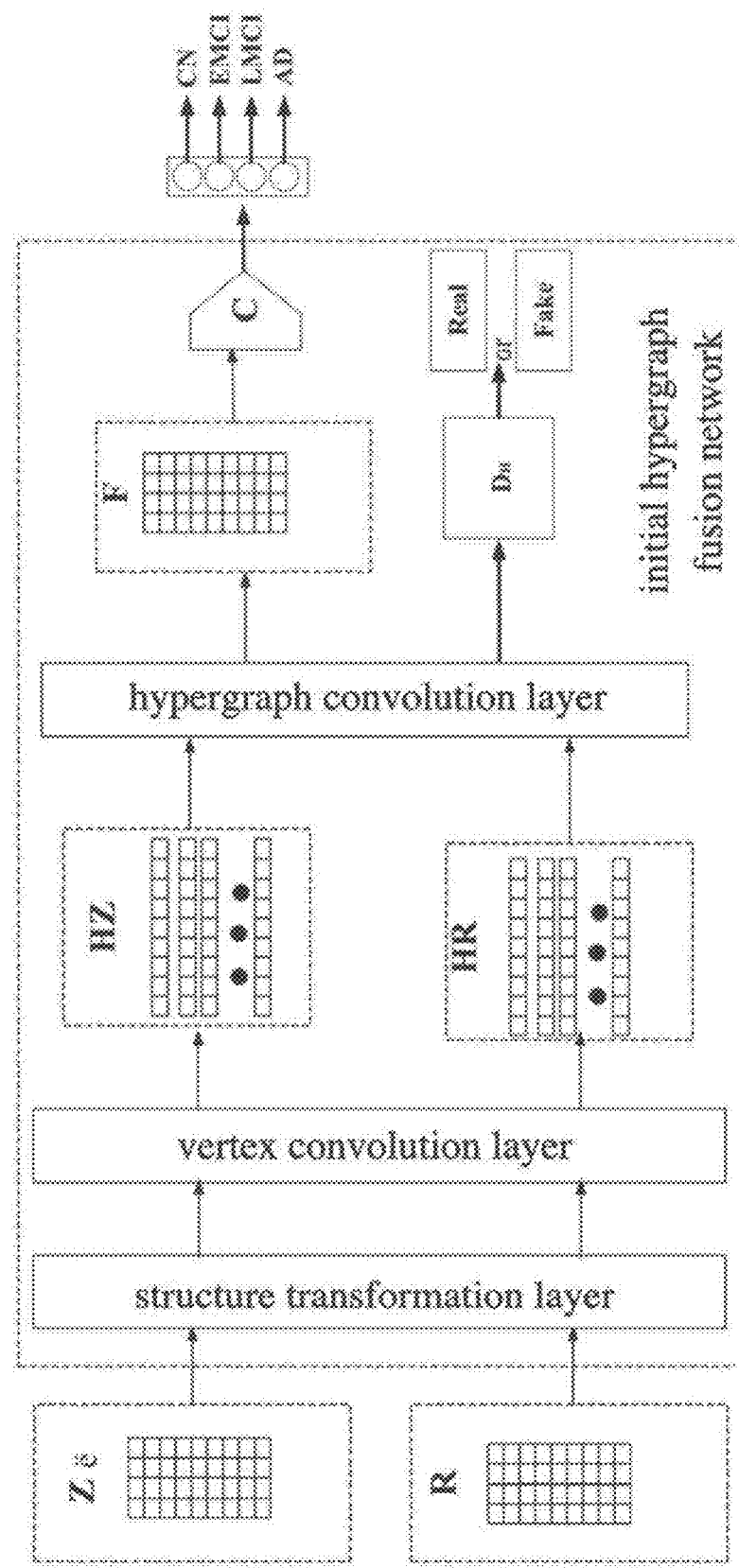
FIG. 7 is a network structure diagram of an initial hypergraph fusion network provided by an embodiment of the present application.

The initial hypergraph fusion network may be as shown in FIG. 7, which includes a structure conversion layer, a vertex convolution layer, a discriminator $D_H$, a hyperedge convolution layer, and a classifier C.

The adversarial collaborative training method provided by the present application is illustrated below by taking a process of training the adversarial generative hypergraph fusion network based on a set of data samples in the training set as an example. This process includes the following.

At S11, preprocess data.

A set of data samples 1 is obtained from a training set, and the DTI data and fMRI data in the data samples 1 are preprocessed to obtain graph data, that is, a node connection matrix A and a node feature matrix X.

Prior probability distribution $P_z$ of the graph data is determined according to the node connection matrix A and the node feature matrix X. A node feature Z of a hidden layer space is obtained by sampling from the prior probability distribution $P_z$.

For example, a submatrix (with a size of s×s, s<m) may be extracted from the node connection matrix A based on a DPP (Determinantal Point Process). Then, eigenvectors corresponding to s functional nodes are extracted from the node feature matrix X to form a feature matrix, and a PCA (Principal Component Analysis) algorithm is used to perform dimension reduction on the feature matrix. Finally, the dimension-reduced feature matrix is calculated through a kernel density estimation algorithm to obtain the prior probability distribution $P_z$ of the graph data.

At S12, input A, X, and Z into a non-Euclidean spatial feature extraction network for training Among them, A and X are input into an encoder, i.e. a GCN model, to extract a node feature representation of the hidden layer space (i.e., a non-Euclidean space feature Z'). Here, A has a size of m×m, X has a size of m×d, Z' has a size of m×q, m is the number of the functional nodes in the brain corresponding to the data samples, d is the length of the node feature of the functional node, and q is the length of the node feature of the hidden layer space.

Z is input into a generator G1 for data reconstruction to obtain a reconstructed node feature matrix X'.

It could be understood that, Z' is a non-Euclidean spatial feature estimated based on the GCN model, Z is a non-Euclidean spatial feature estimated based on the prior probability distribution $P_z$. x is an actual acquired node feature matrix, X' is reconstructed based on Z and based on the generator G1. That is to say, two sets of data from different mapping spaces may be obtained, the first set is (x, Z') from the encoding space, and the second set is (z, X') from the reconstruction space.

At S13, input two sets of data into a discriminator Dxz for discrimination.

At S14, input Z' into a generator G2 for data reconstruction to obtain a reconstructed node feature X'' matrix and a node connection matrix A''.

Based on the above S11-16, firstly the network parameters of the G1, the G2 and the GCN model are kept unchanged, and at this time the first set of data (x, Z') and the second set of data (Z, X') are also unchanged. Through adjusting the network parameters of the discriminator Dxz, the difference between the output results reaches the maximum after the first set of data (X, Z') and the second set of data (Z, X') are input into the discriminator Dxz.

When the first set of data (x, Z') and the second set of data (z, X') are input into the discriminator Dxz and the difference between the output results reaches the maximum, the network parameters of the discriminator Dxz are kept unchanged, and the network parameters of the G1, the G2 and the GCN model are adjusted. The first set of data (x, Z') and the second set of data (z, X') vary with the network parameters of the G1, the G2 and the GCN model.

The first set of data (x, Z') and the second set of data (z, X') are continually input into the discriminator Dxz, when the outputs $D_{xz}(X, Z')$ and $D_{xz}(X', Z)$ of the discriminator Dxz can make a loss value $L_{D_{xz}}(P_x, P_z)$ of the discriminator Dxz meet a preset condition (for example, reaching the minimum or keeping constant), and the outputs $D_{xz}(X, Z')$ and $D_{xz}(X', Z)$ of the discriminator Dxz and the output GCN(X) of the GCN model can make a sum of a loss value $L_{\varepsilon G}(P_x, P_z)$ of the G1 and a loss value $L_{Re}(X)$ of the G2 less than a preset generator loss threshold. As such, the BiGAN model can be determined as converged, and the BiGAN model is trained based on the sample data 1 to complete one time of adversarial training.

In an embodiment of the present application, the loss value $L_{D_{xz}}(P_x, P_z)$ of the discriminator Dxz may be obtained through calculation according to the following formula:

$$L_{D_{xz}}(P_x,P_z) = -E_{x \sim P_x, z' \sim GCN(x)}[D_{xz}(X,Z')] + E_{x' \sim G(z), z \sim P_z}$$
$$[D_{xz}(X',Z)] + \alpha E_{\bar{z} \sim P_{\bar{z}}}[\|\Delta_{\bar{z}} D_{xz}(\bar{z}) - 1\|] + \beta E_{\bar{x} \sim P_{\bar{x}}}[\|\Delta_{\bar{x}}$$
$$D_{xz}(\bar{x}) - 1\|]$$

where, $\bar{Z}$ denotes an interpolation value of cross distribution between GCN(X) and $P_z$. $\bar{X}$ represents an interpolation value of cross distribution between G(Z) and $P_x$, and α and β are weighting coefficients respectively.

The loss value $L_{\varepsilon G}(P_x, P_z)$ of G1 may be obtained through calculation based on the following formula:

$$L_{\varepsilon G}(P_x,P_z) = E_{x \sim P_x, z' \sim GCN(x)}[D_{xz}(X,Z')] - E_{x' \sim G(z), z \sim P_z}[D_{xz}(X',Z)]$$

The loss value $L_{Re}(X)$ of G2 may be obtained through calculation based on the following formula:

$$L_{Re}(X) = E_{x \sim P_x}[s(X,X'')] - E_{x \sim P_x}[s(A,A'')]$$

Where, X''=G(GCN(X)), A''=sigmoid(GCN(X)·GCN(X)$^T$), and s(X,X'')=X log X''+(1−X)log(1−X'').

It is worth noting that, during the adversarial training of the BiGAN model, the distribution curve between the brain connection features and the brain node features is estimated through the graph data to obtain the prior probability distribution $P_z$. Then, the model training is carried out through the prior probability distribution $P_z$ which can speed up the efficiency of model training and can effectively improve the generalization of the BiGAN model.

After the BiGAN model is trained based on the sample data 1, the non-Euclidean spatial feature Z' finally output by the GCN model may be sent to the initial hypergraph fusion network for adversarial training of the initial hypergraph fusion network.

Before performing the above S12-S14, or after performing the above S12-S14, or the following training process for the sMRI feature extraction network may be performed while performing the above S12-S14. It includes the following steps S15-18.

At S15, input the sMRI data into a convolution pooling layer for processing.

Exemplarily, it is assumed that the sMRI data is three-dimensional data, the input size of which is 91×109×91, and the convolution pooling layer includes a convolution layer and a pooling layer. Among them, the convolution layer has a convolution kernel with a size of 7×7×7, and has a stride of 2, and has 56 channels (filters). The sMRI data is input into the convolution layer for processing, and 56 feature maps of the sMRI data are extracted, that is, an output size of the convolution layer is 46×55×46×56. Then, dimension reduction is performed on the feature maps output by the convolution layer by using the pooling layer to obtain primary feature information with a size of 23×28×23×56. Among them, the stride of the pooling layer is equal to 2.

At S16, input the primary feature information into a Densnet module for advanced feature information extraction.

Exemplarily, assuming that the Densnet module includes four block layers and three translation layers. Each block first uses a 1×1×1 convolution kernel to perform dimension reduction on the input features, and then uses a 3×3×3 convolution kernel to extract features, where the 3×3×3 convolution kernel uses a dense connection manner to fuse the features output by previous multiple 3×3×3 convolution layers. Each block is followed by one translation layer, which is used to perform superimposition and dimension reduction on the outputs of all convolution layers in the previous block layer. Exemplarily, the Block A includes four layers, and the Block A has an output size of 23×28×23×168(56+28*4) after the primary feature information is input. The Translation A has an input size of 23×28×23×168, and has an output size of 11×14×11×84. The Block B includes four layers, has an input size of 11×14×11×84 and an output size of 12×14×12×252(84+6*28). The Translation B has an input size of 11×14×11×252, and has an output size of 5×7×5×126. The Block C includes eight layers, and the Block C has an input size of 5×7×5×126 and has an output size of 5×7×5×350(126+8*28). The Translation C has an input size of 5×7×5×350, and has an output size of 2×3×2×175. The Block D includes six layers, and the Block D has an input size of 2×3×2×175 and has an output size of 2×3×2×343(175+6*28). The output of the Block D is the advanced feature information.

At S17, obtain a semantic representation vector v according to the advanced feature information. The advanced feature information is input into a fully connected layer FC1, and the FC1 performs an adaptive global pooling operation on the advanced feature information based on a 2×3×2 pooling kernel to obtain a feature vector with a size of 1×343. Then, the feature vector is input into a fully connected layer FC2 for weighting each dimension to obtain the semantic representation vector with a size of 1×128.

At S18, perform feature weighting and fusing on the semantic representation vector v, and then input it into a Softmax function for operation to output a 1×4 vector, where each value in this vector represents probability of the predicted four disease categories respectively.

If the vector output by the Softmax function is different from the disease category label corresponding to the data sample 1, then the network parameters of the Densnet classification network are adjusted, and returning to S15 to restart the training Until the vector output by the Softmax function of the Densnet classification network is the same as the disease category label corresponding to the data sample 1, at this time it can be determined that the training of the Densnet classification network based on the data sample 1 is completed.

After the training of the Densnet classification network based on the data sample 1 is completed, the FC2 may send the last output semantic representation vector to the Euclidean spatial feature extraction network for the encoding-decoding model to train. The training process of the encoding-decoding model may include the following step S19.

At S19, input v into the encoder for encoding processing to obtain the Euclidean space feature R, and then input R into the decoder for reconstruction to obtain a reconstructed semantic representation vector V'.

The network parameters of the encoding-decoding model are adjusted multiple times (V' varies with the network parameters), until v and V' can make reconstruction loss $L_{De}(X)$ of the encoder and decoder meet a preset condition (for example, less than a preset threshold), that is, the difference between v and V' tends to be stable.

Exemplarily, the reconstruction loss $L_{De}(X)$ of the encoder and decoder may be calculated based on the following formula:

$$L_{De}(X)=E_{V\sim P_V}[s(v,v')]$$

Where, v'=Decoder (Encoder (v)), s(v, v')=v log v'+(1−v)log(1−v').

When the reconstruction loss $L_{De}(X)$ of the encoder and decoder meets the preset condition, and after the training of the encoding-decoding model is completed based on the sample data 1, the encoder may send the final output data R to the initial hypergraph fusion network for adversarial training of the initial hypergraph fusion network. The adversarial training process of the initial hypergraph fusion network includes S20-24.

At S20, receive, by a graph structure transformation layer, the non-Euclidean spatial feature Z' from the GCN model and the Euclidean spatial feature R from the encoder. The graph structure transformation layer transforms Z' into a first hypergraph matrix $G_z$ with a size of m×m and transforms R into a second hypergraph matrix $G_R$ with a size of m×m through the KNN algorithm.

At S21, respectively input the $G_z$ and $G_R$ into a vertex convolution layer, and calculate a first hyperedge feature $H_z$ of $G_z$ and a second hyperedge feature $H_R$ of $G_R$ respectively according to the following formula.

$$H=D_e^{-1/2}G^TD_e^{-1/2}YW$$

At S22, input $H_z$ and $H_R$ into a discriminator $D_H$, and conduct adversarial training on $H_z$ and $H_R$ through learning data distribution of different hyperedges by $D_H$ to identify whether the non-Euclidean spatial feature Z' from the GCN model and the Euclidean spatial feature R from the encoder are in the same feature distribution.

Based on the above S21-22, firstly W is kept unchanged, and at this time and $H_z$ and $H_R$ are also remain unchanged. By adjusting the network parameters of the discriminator $D_H$, the difference between the output results reaches the maximum after $H_z$ and $H_R$ are input into the discriminator $D_H$.

When the difference between the output results reaches the maximum after $H_z$ and $H_R$ are input into the discriminator $D_H$, the network parameters of the discriminator $D_H$ are kept unchanged, and W is adjusted and steps S35-36 are executed. and $H_z$ and $H_R$ varies with W.

Among them, $D_H$ is an adversarial discriminator, through performing adversarial training on $H_z$ and $H_R$ the problem of inconsistent data space distribution between the non-Euclidean spacial feature Z' and the Euclidean spacial feature R can be solved, so that the accuracy of the fused feature F can be improved.

At S23, input $H_z$ and $H_R$ into a hyperedge convolution layer for performing hyperedge convolution calculation on the obtained $H_z$ and $H_R$ to obtain the fused feature F (with a size of m×d) of Z' and R.

$$F=D_v^{-1/2}G^T D_v^{-1/2}H'$$

At S24, input F into a classifier C, and perform feature fusion on F by the classifier C to output a four-category vector.

$H_z$ and $H_R$ are continually input into the discriminator $D_H$. When the outputs $D_H(x)$ and $D_H(z)$ of the discriminator Dxz can make a loss value $L_{D_H}(P_x, P_z)$ of the discriminator $D_H$ meet a preset condition (for example, reaching the minimum or remaining unchanged), and the output $D_H(Z)$ of the discriminator $D_H$ can make a loss value $L_{H_R}(P_z)]$ of the vertex convolution layer remain unchanged, and F can make a loss value $L_C(F, Q)$ of the classifier reach the minimum or remain unchanged, then it is determined that the primary hypergraph fusion network has completed the adversarial training one time based on the sample data 1.

Exemplarily, the loss value of the classifier C may be calculated through the following formula:

$$L_C(F,Q)=E_{F\sim P_F}[s(F,Q)]$$

Here, the loss value of the discriminator $D_H$ may be calculated through the following formula:

$$L_{D_H}(P_X, P_Z) = -E_{x \sim P_{H_Z}}[D_H(x)] + E_{Z \sim P_{H_R}}[D_H(z)]$$

The loss value $L_{H_R}(P_z)]$ of the vertex convolution layer may be calculated through the following formula:

$$L_{H_R}(P_Z) = -E_{Z \sim P_{H_R}}[D_H(z)]$$

After the training is completed by using the sample data 1, other sample data in the training set may be selected to continue training until the adversarial generative hypergraph fusion network converges and the training is completed.

After the training of the adversarial generative hypergraph fusion network is completed, a part network structure in the adversarial generative hypergraph fusion network may be migrated to obtain the fusion network. For example, the generator G1, the generator G2 and the discriminator Dxz in the non-Euclidean spatial feature extraction network are migrated, the Softmax function in the sMRI feature extraction network is migrated, the decoder in the encoding-decoding model is migrated, and the discriminator $D_H$ in the initial hypergraph fusion network is migrated. After migration, the remaining network structures in the adversarial generative hypergraph fusion network constitute the fusion network provided by the present application.

It should be noted that the execution subject of the above training process may be the same device as the terminal device running the fusion network, or may be other computer devices, which is not limited in the present application.

Based on this fusion network, through mapping the features of different spaces into the hypergraph data structure, and using the hypergraph convolution strategy to fuse the features of different spaces, the possible heterogeneity between the features of different spaces is avoided, so that the complementary fused features of between multi-modal data can be acquired.

Based on the same inventive concept, as an implementation of the above method, embodiments of the present application provide an image-driven brain atlas construction apparatus, and the apparatus embodiments correspond to the foregoing method embodiments, and the details in the foregoing method embodiments will not be described one by one in the apparatus embodiments for facilitating reading, but it should be clear that the apparatus in these embodiments can correspondingly implement all the content in the foregoing method embodiments.

Figure 8:
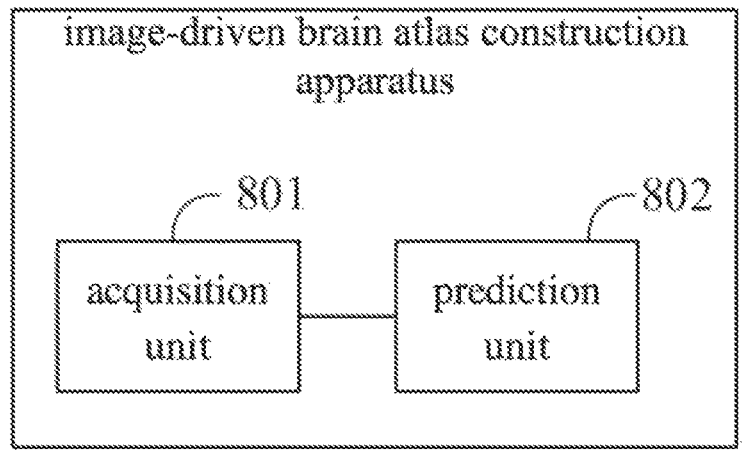
FIG. 8 is a structural schematic diagram of an image-driven brain atlas construction apparatus provided by an embodiment of the present application.

As shown in FIG. 8, the present application provides an image-driven brain atlas construction apparatus, which includes:

an acquisition unit 801 configured to acquire multi-modal data of a brain to be predicted, where the multi-modal data is acquired according to image data collected when the brain is under at least three different modalities;

a prediction unit 802 configured to input the multi-modal data into a preset fusion network for processing to output and acquire feature parameters of the brain; where the processing of the multi-modal data by the fusion network includes: extracting a non-Euclidean spacial feature and an Euclidean spacial feature of the multi-modal data, and performing hypergraph fusion on the non-Euclidean spacial feature and the Euclidean spacial feature to acquire the feature parameters, where the feature parameters are used to characterize a brain connection matrix and/or a disease category of the brain.

Optionally, performing, by the prediction unit 802, hypergraph fusion on the non-Euclidean spacial feature and the Euclidean spacial feature to acquire the feature parameters includes: performing hypergraph data transformation on the non-Euclidean spacial feature and the Euclidean spacial feature respectively to acquire a first hypergraph matrix and a second hypergraph matrix; performing vertex convolution calculation on the first hypergraph matrix and the second hypergraph matrix respectively to acquire a first hyperedge feature and a second hyperedge feature; performing hyperedge convolution calculation on the first hyperedge feature and the second hyperedge feature to obtain a fused feature; and acquiring the feature parameters according to the fused feature.

Optionally, performing, by the prediction unit 802, hyperedge convolution calculation on the first hyperedge feature and the second hyperedge feature to obtain a fused feature includes: merging the first hyperedge feature with the second hyperedge feature to acquire a merged matrix; performing hyperedge convolution calculation on the merged matrix to obtain the fused feature.

Optionally, the image data includes sMRI data, DTI data and fMRI data of the brain; the multi-modal data includes a node connection matrix acquired according to the DTI data, and a node feature matrix acquired according to the fMRI data, and the sMRI data.

Optionally, extracting, by the prediction unit 802, the non-Euclidean spatial feature of the multi-modal data includes: performing graph convolution processing on the node connection matrix and the node feature matrix to obtain the non-Euclidean spatial feature.

Optionally, extracting, by the prediction unit 802, the Euclidean spatial feature of the multi-modal data includes: performing convolution processing on the sMRI data to acquire a semantic representation vector; encoding the semantic representation vector to acquire the Euclidean spatial feature.

Optionally, the image-driven brain atlas construction apparatus further includes:

- a training apparatus 803 configured to: acquire data samples, where the data samples include sMRI data, DTI data, fMRI data of a sample brain and disease category labels of the sample brain; acquire a node feature matrix, a node connection matrix and a prior probability distribution of the sample brain according to the fMRI data and the DTI data of the sample brain; acquire a node feature of a hidden layer space from the prior probability distribution through sampling; conduct adversarial training on a preset adversarial generative hypergraph fusion network by using the node feature of the hidden layer space, the node feature matrix, the node connection matrix and the sMRI data of the sample brain; when the adversarial generative hypergraph fusion network converges, perform migration processing on the adversarial generative hypergraph fusion network to acquire the fusion network.

The image-driven brain atlas construction apparatus provided in this embodiment can execute the above method embodiments, and their implementation principles and technical effects are similar, and details of which will not be repeated herein again.

Those skilled in the art can clearly understand that, for the convenience and simplicity of description, the division of the above-mentioned functional units and modules is only used as an example for illustration. In practical applications, the above-mentioned functions can be allocated to different functional units or module for completion according to needs, that is, the internal structure of the apparatus is divided into different functional units or modules to complete all or part of the functions described above. Each functional unit or module in the embodiments may be integrated in one processing unit, or each unit may exist physically alone, or two or more units may be integrated into one unit, and the above-mentioned integrated unit may be implemented in a form of hardware or in a form of software functional unit. In addition, the specific names of the functional units and modules are only for the convenience of distinguishing each other, and are not used to limit the protection scope of the present application. For the specific working processes of the units and modules in the above-mentioned system, reference may be made to the corresponding processes in the foregoing method embodiments, which will not be repeated herein again.

Figure 9:
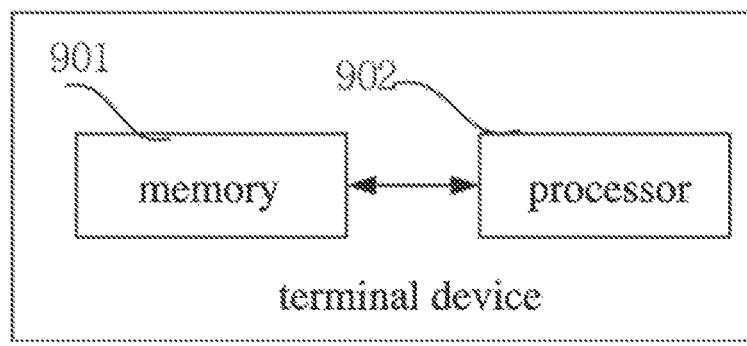
FIG. 9 is a structural schematic diagram of a terminal device provided by an embodiment of the present application.

Based on the same inventive concept, an embodiment of the present application further provides a terminal device. FIG. 9 is a structural schematic diagram of a terminal device provided by an embodiment of the present application. As shown in FIG. 9, the terminal device provided by this embodiment includes: a memory 901 and a processor 902, where the memory 901 is configured to store a computer program; the processor 902 is configured to implement the methods described in the above method embodiments when invoking the computer program.

The terminal device provided in this embodiment may implement the foregoing method embodiments, and their implementation principles and technical effects are similar, and details of which are not described herein again.

Embodiments of the present application further provide a computer-readable storage medium on which a computer program is stored, and the computer program, when executed by a processor, realizes the methods described in the foregoing method embodiments.

Embodiments of the present application further provide a computer program product, when the computer program product runs on a terminal device, the computer program product causes the terminal device to execute and implement the methods described in the foregoing method embodiments.

Embodiments of the present application further provide a chip system, which includes a processor coupled to a memory, and the processor executes a computer program stored in the memory to implement the methods described in the foregoing method embodiments. Here, the chip system may be a single chip or a chip module composed of multiple chips.

If the above-mentioned integrated unit is implemented in the form of software functional unit and sold or used as an independent product, it may be stored in a computer-readable storage medium. Based on this understanding, all or part of the processes in the methods of the above embodiments can be implemented through instructing relevant hardware by a computer program, and the computer program may be stored in the computer-readable storage medium, and the computer program, when executed by a processor, may implements the steps of each of the above method embodiments. Here, the computer program includes a computer program code, and the computer program code may be in a form of a source code, an object code, an executable file or some intermediate form, and the like. The computer-readable storage medium may include at least: any entity or apparatus capable of carrying the computer program code to a photographing apparatus/terminal device, recording medium, computer memory, ROM (Read-Only Memory), RAM (Random Access Memory), electrical carrier signal, telecommunication signal and software distribution medium. For example, a U disk, a mobile hard disk, a magnetic disk or a CD, etc. In some jurisdictions, according to legislation and patent practice, the computer-readable medium can not be the electrical carrier signal and telecommunications signal.

In the foregoing embodiments, the description for each embodiment has its own emphasis. For parts that are not described or described in detail in a certain embodiment, reference may be made to the relevant descriptions of other embodiments.

Those of ordinary skill in the art should realize that the units and algorithm steps of each example described in conjunction with the embodiments disclosed herein may be implemented by electronic hardware, or a combination of computer software and electronic hardware. Whether these functions are performed by hardware or software depends on specific applications and design constraints of the technical solution. Those skilled in the art may implement the described functions by using different methods for each particular application, but such implementations should not be considered beyond the scope of the present application.

In the embodiments provided in the present application, it should be understood that the disclosed apparatus/device and method may be implemented in other manners. For example, the apparatus/device embodiments described above are only illustrative. For example, the division of the modules or units is only a logical function division, and there may be other division methods in actual implementations, for example, multiple units or components may be combined or may be integrated into another system, or some features may be omitted or not implemented. On another perspective, the shown or discussed mutual coupling or direct coupling or communication connection may be indirect coupling or communication connection of devices or units through some interfaces, and may be in an electrical form, a mechanical form or other forms.

It should be understood that, when used in this specification and the appended claims of the present application, the term "comprising" indicates the presence of the described feature, entity, step, operation, element and/or component, but does not exclude the presence or addition of one or more other features, entities, steps, operations, elements, components and/or sets thereof.

It should also be understood that, the term "and/or" used in this specification and the appended claims of the present application refers to any combination and all possible combinations of one or more of the associated listed items, and includes these combinations.

As used in this specification and the appended claims of the present application, the term "if" may be contextually interpreted as "when" or "once" or "in response to determination of . . . " or "in response to detection of . . . ". Similarly, the phrases "if . . . is determined" or "if [the described condition or event] is detected" may be contextually interpreted to mean "once . . . is determined" or "in response to determination of . . . " or "once [the described condition or event] is detected]" or "in response to detection of [the described condition or event]".

In addition, in the description of this specification and the appended claims of the present application, the terms "first", "second", "third", etc. are only used to distinguish the description, and should not be construed as indication or implication of relative importance.

References in this specification of the present application to "one embodiment" or "some embodiments" and the like mean that one or more embodiments of the present application include a particular feature, structure or characteristic described in connection with this embodiment. Thus, the phrases "in one embodiment," "in some embodiments," "in some other embodiments," "in other embodiments," etc. appeared at different places of this specification are not necessarily all refer to the same embodiment, but mean "one or more but not all embodiments", unless additionally and specifically emphasized otherwise. The terms "including", "comprising", "having" and variations thereof mean "including but being not limited to", unless additionally and specifically emphasized otherwise.

Finally, it should be noted that the above embodiments are only used to illustrate, but not to limit, the technical solutions of the present application; although the present application has been described in detail with reference to the foregoing embodiments, those of ordinary skill in the art should understand that: they can still modify the technical solutions described in the foregoing embodiments, or equivalently replace some or all of the technical features in the technical solutions described in the foregoing embodiments; and these modifications or replacements do not make the essence of the corresponding technical solutions deviate from the scope of the technical solutions of the embodiments of the present application.

What is claimed is:

1. An image-driven brain atlas construction method, comprising:
   acquiring multi-modal data of a brain to be predicted, wherein the multi-modal data is acquired according to image data collected when the brain is under at least three different modalities;
   inputting the multi-modal data into a preset fusion network for processing to output and acquire feature parameters of the brain; wherein the processing of the multi-modal data by the fusion network comprises: extracting a non-Euclidean spacial feature and an Euclidean spacial feature of the multi-modal data, and performing hypergraph fusion on the non-Euclidean spacial feature and the Euclidean spacial feature to acquire the feature parameters, wherein the feature parameters are used to characterize a brain connection matrix and/or a disease category of the brain.

2. The method of claim 1, wherein, the performing hypergraph fusion on the non-Euclidean spacial feature and the Euclidean spacial feature to acquire the feature parameters comprises:
   performing hypergraph data transformation on the non-Euclidean spacial feature and the Euclidean spacial feature respectively to acquire a first hypergraph matrix and a second hypergraph matrix;
   performing vertex convolution calculation on the first hypergraph matrix and the second hypergraph matrix respectively to acquire a first hyperedge feature and a second hyperedge feature;
   performing hyperedge convolution calculation on the first hyperedge feature and the second hyperedge feature to acquire a fused feature;
   acquiring the feature parameters according to the fused feature.

3. The method of claim 2, wherein, the performing hyperedge convolution calculation on the first hyperedge feature and the second hyperedge feature to acquire a fused feature comprises:
   merging the first hyperedge feature with the second hyperedge feature to acquire a merged matrix;
   performing hyperedge convolution calculation on the merged matrix to acquire the fused feature.

4. The method of claim 3, wherein, the extracting the non-Euclidean spatial feature of the multi-modal data comprises:
   performing graph convolution processing on the node connection matrix and the node feature matrix to acquire the non-Euclidean spatial feature.

5. The method of claim 3, wherein, the extracting the Euclidean spatial feature of the multi-modal data comprises:
   performing convolution processing on the sMRI data to acquire a semantic representation vector;
   encoding the semantic representation vector to acquire the Euclidean spatial feature.

6. The method of claim 1, wherein, the image data comprises sMRI data, DTI data and fMRI data of the brain; the multi-modal data comprises a node connection matrix acquired according to the DTI data, a node feature matrix acquired according to the fMRI data and the sMRI data.

7. The method of claim 6, wherein, the method further comprises:
acquiring data samples, wherein the data samples include sMRI data, DTI data, fMRI data of a sample brain and disease category labels of the sample brain;
acquiring a node feature matrix, a node connection matrix and a prior probability distribution of the sample brain according to the fMRI data and the DTI data of the sample brain;
acquiring a node feature of a hidden layer space from the prior probability distribution through sampling;
conducting adversarial training on a preset adversarial generative hypergraph fusion network by using the node feature of the hidden layer space, the node feature matrix, the node connection matrix and the sMRI data of the sample brain;
when the adversarial generative hypergraph fusion network converges, performing migration processing on the adversarial generative hypergraph fusion network to acquire the fusion network.

8. A terminal device, comprising a memory, a processor and a computer program stored in the memory and executable on the processor, wherein, the processor, when executing the computer program, implements:
acquiring multi-modal data of a brain to be predicted, wherein the multi-modal data is acquired according to image data collected when the brain is under at least three different modalities;
inputting the multi-modal data into a preset fusion network for processing to output and acquire feature parameters of the brain; wherein the processing of the multi-modal data by the fusion network comprises: extracting a non-Euclidean spacial feature and an Euclidean spacial feature of the multi-modal data, and performing hypergraph fusion on the non-Euclidean spacial feature and the Euclidean spacial feature to acquire the feature parameters, wherein the feature parameters are used to characterize a brain connection matrix and/or a disease category of the brain.

9. The terminal device of claim 8, wherein, the performing hypergraph fusion on the non-Euclidean spacial feature and the Euclidean spacial feature to acquire the feature parameters comprises:
performing hypergraph data transformation on the non-Euclidean spacial feature and the Euclidean spacial feature respectively to acquire a first hypergraph matrix and a second hypergraph matrix;
performing vertex convolution calculation on the first hypergraph matrix and the second hypergraph matrix respectively to acquire a first hyperedge feature and a second hyperedge feature;
performing hyperedge convolution calculation on the first hyperedge feature and the second hyperedge feature to acquire a fused feature;
acquiring the feature parameters according to the fused feature.

10. The terminal device of claim 9, wherein, the performing hyperedge convolution calculation on the first hyperedge feature and the second hyperedge feature to acquire a fused feature comprises:
merging the first hyperedge feature with the second hyperedge feature to acquire a merged matrix;
performing hyperedge convolution calculation on the merged matrix to acquire the fused feature.

11. The terminal device of claim 10, wherein, the extracting the non-Euclidean spatial feature of the multi-modal data comprises:
performing graph convolution processing on the node connection matrix and the node feature matrix to acquire the non-Euclidean spatial feature.

12. The terminal device of claim 10, wherein, the extracting the Euclidean spatial feature of the multi-modal data comprises:
performing convolution processing on the sMRI data to acquire a semantic representation vector;
encoding the semantic representation vector to acquire the Euclidean spatial feature.

13. The terminal device of claim 8, wherein, the image data comprises sMRI data, DTI data and fMRI data of the brain;
the multi-modal data comprises a node connection matrix acquired according to the DTI data, a node feature matrix acquired according to the fMRI data and the sMRI data.

14. The terminal device of claim 13, wherein, the processor, when executing the computer program, further implements:
acquiring data samples, wherein the data samples include sMRI data, DTI data, fMRI data of a sample brain and disease category labels of the sample brain;
acquiring a node feature matrix, a node connection matrix and a prior probability distribution of the sample brain according to the fMRI data and the DTI data of the sample brain;
acquiring a node feature of a hidden layer space from the prior probability distribution through sampling;
conducting adversarial training on a preset adversarial generative hypergraph fusion network by using the node feature of the hidden layer space, the node feature matrix, the node connection matrix and the sMRI data of the sample brain;
when the adversarial generative hypergraph fusion network converges, performing migration processing on the adversarial generative hypergraph fusion network to acquire the fusion network.

15. A non-transitory computer-readable storage medium on which a computer program is stored, wherein, the computer program, when executed by a processor, implements:
acquiring multi-modal data of a brain to be predicted, wherein the multi-modal data is acquired according to image data collected when the brain is under at least three different modalities;
inputting the multi-modal data into a preset fusion network for processing to output and acquire feature parameters of the brain; wherein the processing of the multi-modal data by the fusion network comprises: extracting a non-Euclidean spacial feature and an Euclidean spacial feature of the multi-modal data, and performing hypergraph fusion on the non-Euclidean spacial feature and the Euclidean spacial feature to acquire the feature parameters, wherein the feature parameters are used to characterize a brain connection matrix and/or a disease category of the brain.

16. The non-transitory computer-readable storage medium of claim 15, wherein, the performing hypergraph fusion on the non-Euclidean spacial feature and the Euclidean spacial feature to acquire the feature parameters comprises:
performing hypergraph data transformation on the non-Euclidean spacial feature and the Euclidean spacial feature respectively to acquire a first hypergraph matrix and a second hypergraph matrix;

performing vertex convolution calculation on the first hypergraph matrix and the second hypergraph matrix respectively to acquire a first hyperedge feature and a second hyperedge feature;

performing hyperedge convolution calculation on the first hyperedge feature and the second hyperedge feature to acquire a fused feature;

acquiring the feature parameters according to the fused feature.

17. The non-transitory computer-readable storage medium of claim 16, wherein, the performing hyperedge convolution calculation on the first hyperedge feature and the second hyperedge feature to acquire a fused feature comprises:

merging the first hyperedge feature with the second hyperedge feature to acquire a merged matrix;

performing hyperedge convolution calculation on the merged matrix to acquire the fused feature.

18. The non-transitory computer-readable storage medium of claim 17, wherein, the extracting the non-Euclidean spatial feature of the multi-modal data comprises:

performing graph convolution processing on the node connection matrix and the node feature matrix to acquire the non-Euclidean spatial feature.

19. The non-transitory computer-readable storage medium of claim 17, wherein, the extracting the Euclidean spatial feature of the multi-modal data comprises:

performing convolution processing on the sMRI data to acquire a semantic representation vector;

encoding the semantic representation vector to acquire the Euclidean spatial feature.

20. The non-transitory computer-readable storage medium of claim 15, wherein, the image data comprises sMRI data, DTI data and fMRI data of the brain;

the multi-modal data comprises a node connection matrix acquired according to the DTI data, a node feature matrix acquired according to the fMRI data and the sMRI data.

\* \* \* \* \*